United States Patent
Hsu et al.

(10) Patent No.: US 10,849,702 B2
(45) Date of Patent: Dec. 1, 2020

(54) USER INPUT DEVICES FOR CONTROLLING MANIPULATION OF GUIDEWIRES AND CATHETERS

(71) Applicant: Auris Health, Inc., Redwood City, CA (US)

(72) Inventors: Jason Joseph Hsu, Mountain View, CA (US); June Park, Palo Alto, CA (US); Ruchi Choksi Bhatt, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 754 days.

(21) Appl. No.: 13/835,978

(22) Filed: Mar. 15, 2013

(65) Prior Publication Data

US 2014/0276938 A1 Sep. 18, 2014

(51) Int. Cl.
*A61B 34/00* (2016.01)
*A61B 34/30* (2016.01)

(52) U.S. Cl.
CPC .............. *A61B 34/76* (2016.02); *A61B 34/30* (2016.02); *A61B 2034/301* (2016.02); *A61B 2034/742* (2016.02)

(58) Field of Classification Search
CPC .............. A61B 19/20; A61B 19/2203; A61B 2019/2223; A61B 2019/2242; A61B 2019/2292; A61B 34/30; A61B 34/76; A61B 2034/301; A61B 2034/742
USPC ....................................... 606/1, 130
See application file for complete search history.

(56) References Cited

U.S. PATENT DOCUMENTS

| | | | |
|---|---|---|---|
| 4,771,262 | A | 9/1988 | Reuss |
| 4,896,554 | A | 1/1990 | Culver |
| 5,008,528 | A | 4/1991 | Duchon |
| 5,176,310 | A | 1/1993 | Akiyama et al. |
| 5,280,781 | A | 1/1994 | Oku |
| 5,398,691 | A | 3/1995 | Martin et al. |
| 5,408,409 | A | 4/1995 | Glassman et al. |
| 5,499,632 | A | 3/1996 | Hill et al. |
| 5,524,180 | A | 6/1996 | Wang |
| 5,526,812 | A | 6/1996 | Dumoulin et al. |
| 5,631,973 | A | 5/1997 | Green |
| 5,713,946 | A | 2/1998 | Ben-Haim |
| 5,749,362 | A | 5/1998 | Funda et al. |
| 5,762,458 | A | 6/1998 | Wang et al. |

(Continued)

FOREIGN PATENT DOCUMENTS

| | | |
|---|---|---|
| EP | 1 800 593 | 6/2007 |
| EP | 2 158 834 | 3/2010 |

(Continued)

*Primary Examiner* — Gary Jackson
*Assistant Examiner* — Sebastian X Lukjan
(74) *Attorney, Agent, or Firm* — Knobbe, Martens, Olson & Bear LLP

(57) ABSTRACT

A robotic surgical system with an input device has two operational modes by which both steerable and non-steerable elongate instruments can be effectively controlled, such as steerable catheters which can move in at least three orthogonal axes and non-steerable guidewires which can move via axial insertion/retraction or axial rotation. The robotic surgical system may include mapping schemes and haptic feedback to enhance the functionality, operation and ease of use of the input device when controlling non-steerable elongate instruments such as guidewires.

20 Claims, 7 Drawing Sheets

(56) References Cited

U.S. PATENT DOCUMENTS

| | | | |
|---|---|---|---|
| 5,831,614 A | 11/1998 | Tognazzini et al. |
| 5,859,934 A | 1/1999 | Green |
| 5,876,325 A | 3/1999 | Mizuno et al. |
| 5,899,851 A | 5/1999 | Koninckx |
| 5,951,475 A | 9/1999 | Gueziec et al. |
| 5,963,770 A | 10/1999 | Eakin |
| 6,007,550 A | 12/1999 | Wang et al. |
| 6,016,439 A | 1/2000 | Acker |
| 6,038,467 A | 3/2000 | De Bliek et al. |
| 6,096,004 A | 8/2000 | Meglan |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,425,865 B1 | 7/2002 | Salcudean et al. |
| 6,466,198 B1 | 10/2002 | Feinstein |
| 6,468,265 B1 | 10/2002 | Evans et al. |
| 6,516,421 B1 | 2/2003 | Peters |
| 6,690,964 B2 | 2/2004 | Beiger et al. |
| 6,726,675 B1 | 4/2004 | Beyar |
| 6,856,827 B2 | 2/2005 | Seeley et al. |
| 7,155,315 B2 | 12/2006 | Niemeyer et al. |
| 7,594,925 B2 | 9/2009 | Danek |
| 8,021,326 B2 | 9/2011 | Moll et al. |
| 8,180,114 B2 | 5/2012 | Nishihara et al. |
| 8,718,837 B2 | 5/2014 | Wang et al. |
| 8,894,610 B2 | 11/2014 | MacNamara et al. |
| 8,971,597 B2 | 3/2015 | Zhao et al. |
| 9,014,851 B2 | 4/2015 | Wong et al. |
| 9,057,600 B2 | 6/2015 | Walker et al. |
| 9,138,166 B2 | 9/2015 | Wong et al. |
| 9,241,767 B2 | 1/2016 | Prisco et al. |
| 9,283,046 B2 | 3/2016 | Walker et al. |
| 9,289,578 B2 | 3/2016 | Walker et al. |
| 9,498,291 B2 | 11/2016 | Balaji et al. |
| 9,503,681 B1 | 11/2016 | Popescu et al. |
| 9,504,604 B2 | 11/2016 | Alvarez |
| 9,532,840 B2 | 1/2017 | Wong et al. |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 10,016,900 B1 | 7/2018 | Meyer et al. |
| 10,022,192 B1 | 7/2018 | Ummalaneni |
| 10,123,755 B2 | 11/2018 | Walker et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,159,532 B1 | 12/2018 | Ummalaneni et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,346,976 B2 | 7/2019 | Averbuch |
| 10,482,599 B2 | 11/2019 | Mintz et al. |
| 2002/0077533 A1 | 6/2002 | Bieger et al. |
| 2002/0120188 A1 | 8/2002 | Brock et al. |
| 2002/0161280 A1 | 10/2002 | Chatenever et al. |
| 2004/0047044 A1 | 3/2004 | Dalton |
| 2004/0263535 A1 | 12/2004 | Birkenbach et al. |
| 2005/0085714 A1 | 4/2005 | Foley et al. |
| 2005/0193451 A1 | 9/2005 | Quistgaard et al. |
| 2006/0025676 A1 | 2/2006 | Viswanathan et al. |
| 2006/0079745 A1 | 4/2006 | Viswanathan et al. |
| 2006/0095022 A1 | 5/2006 | Moll et al. |
| 2006/0146010 A1 | 7/2006 | Schneider |
| 2006/0173290 A1 | 8/2006 | Lavallee et al. |
| 2007/0083098 A1 | 4/2007 | Stern et al. |
| 2007/0138992 A1* | 6/2007 | Prisco .................... A61B 19/22 |
| | | 318/568.21 |
| 2007/0144298 A1* | 6/2007 | Miller .................... B25J 9/1676 |
| | | 74/490.01 |
| 2007/0185486 A1 | 8/2007 | Hauck |
| 2008/0027313 A1 | 1/2008 | Shachar |
| 2008/0097465 A1 | 4/2008 | Rollins et al. |
| 2008/0108870 A1 | 5/2008 | Wiita et al. |
| 2008/0140087 A1 | 6/2008 | Barbagli et al. |
| 2008/0159653 A1 | 7/2008 | Dunki-Jacobs et al. |
| 2008/0183068 A1 | 7/2008 | Carls et al. |
| 2008/0183188 A1 | 7/2008 | Carls et al. |
| 2008/0306490 A1 | 12/2008 | Lakin et al. |
| 2009/0137952 A1 | 5/2009 | Ramamurthy |
| 2009/0248036 A1 | 10/2009 | Hoffman et al. |
| 2009/0259230 A1 | 10/2009 | Khadem |
| 2009/0259412 A1 | 10/2009 | Brogardh |
| 2009/0326322 A1 | 12/2009 | Diolaiti |
| 2009/0326556 A1* | 12/2009 | Diolaiti .............. A61B 1/00009 |
| | | 606/130 |
| 2010/0019890 A1* | 1/2010 | Helmer et al. ............. 340/407.1 |
| 2010/0039506 A1 | 2/2010 | Sarvestani et al. |
| 2010/0076263 A1 | 3/2010 | Tanaka |
| 2010/0121269 A1 | 5/2010 | Goldenberg |
| 2010/0125284 A1* | 5/2010 | Tanner et al. .................. 606/130 |
| 2010/0161129 A1* | 6/2010 | Costa et al. .................. 700/259 |
| 2010/0204613 A1 | 8/2010 | Rollins et al. |
| 2010/0225209 A1 | 9/2010 | Goldberg |
| 2010/0286847 A1 | 11/2010 | Cerchie et al. |
| 2010/0328455 A1 | 12/2010 | Nam et al. |
| 2011/0021926 A1 | 1/2011 | Spencer |
| 2011/0113852 A1* | 5/2011 | Prisco ........................... 73/1.15 |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1* | 3/2012 | Diolaiti .............. A61B 1/00163 |
| | | 606/130 |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1* | 6/2012 | Sandhu .................. A61B 34/30 |
| | | 606/130 |
| 2012/0191107 A1 | 7/2012 | Tanner et al. |
| 2012/0203067 A1 | 8/2012 | Higgins et al. |
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0028554 A1 | 1/2013 | Wong et al. |
| 2013/0030363 A1 | 1/2013 | Wong et al. |
| 2013/0060146 A1 | 3/2013 | Yang et al. |
| 2013/0165854 A1 | 6/2013 | Sandhu et al. |
| 2013/0317519 A1 | 11/2013 | Romo et al. |
| 2014/0111457 A1 | 4/2014 | Briden et al. |
| 2014/0142591 A1 | 5/2014 | Alvarez et al. |

(56) References Cited

U.S. PATENT DOCUMENTS

| | | |
|---|---|---|
| 2014/0148759 A1 | 5/2014 | Macnamara et al. |
| 2014/0222204 A1 | 8/2014 | Kawashima |
| 2014/0257334 A1 | 9/2014 | Wong et al. |
| 2014/0264081 A1 | 9/2014 | Walker et al. |
| 2014/0275985 A1 | 9/2014 | Walker et al. |
| 2014/0276392 A1 | 9/2014 | Wong et al. |
| 2014/0276394 A1 | 9/2014 | Wong et al. |
| 2014/0276646 A1 | 9/2014 | Wong et al. |
| 2014/0276934 A1 | 9/2014 | Balaji et al. |
| 2014/0276936 A1 | 9/2014 | Kokish et al. |
| 2014/0276937 A1 | 9/2014 | Wong et al. |
| 2014/0276938 A1 | 9/2014 | Hsu |
| 2014/0277333 A1 | 9/2014 | Lewis et al. |
| 2014/0277334 A1 | 9/2014 | Yu et al. |
| 2014/0277747 A1 | 9/2014 | Walker et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0018622 A1 | 1/2015 | Tesar et al. |
| 2015/0051592 A1 | 2/2015 | Kintz |
| 2015/0101442 A1 | 4/2015 | Romo |
| 2015/0105747 A1 | 4/2015 | Rollins et al. |
| 2015/0119638 A1 | 4/2015 | Yu et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0193946 A1 | 7/2015 | Wong et al. |
| 2015/0223902 A1 | 8/2015 | Walker et al. |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0314110 A1 | 11/2015 | Park |
| 2015/0327939 A1 | 11/2015 | Kokish et al. |
| 2015/0335480 A1 | 11/2015 | Alvarez et al. |
| 2015/0375399 A1 | 12/2015 | Chiu et al. |
| 2016/0001038 A1 | 1/2016 | Romo et al. |
| 2016/0007881 A1 | 1/2016 | Wong et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0175059 A1 | 6/2016 | Walker et al. |
| 2016/0183841 A1 | 6/2016 | Duindam et al. |
| 2016/0202053 A1 | 7/2016 | Walker et al. |
| 2016/0213436 A1 | 7/2016 | Inoue |
| 2016/0213884 A1 | 7/2016 | Park |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0065356 A1 | 3/2017 | Balaji et al. |
| 2017/0065364 A1 | 3/2017 | Schuh et al. |
| 2017/0065365 A1 | 3/2017 | Schuh |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0113019 A1 | 4/2017 | Wong et al. |
| 2017/0119413 A1 | 5/2017 | Romo |
| 2017/0119481 A1 | 5/2017 | Romo et al. |
| 2017/0143429 A1 | 5/2017 | Richmond et al. |
| 2017/0151027 A1 | 6/2017 | Walker et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0078321 A1 | 3/2018 | Liao |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0151032 A1 | 5/2019 | Mustufa et al. |
| 2019/0167361 A1 | 6/2019 | Walker et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |

FOREIGN PATENT DOCUMENTS

| | | |
|---|---|---|
| WO | 03086190 A1 | 10/2003 |
| WO | WO 08/049088 | 4/2008 |
| WO | WO 10/025522 | 3/2010 |

\* cited by examiner

USER INPUT DEVICES FOR CONTROLLING MANIPULATION OF GUIDEWIRES AND CATHETERS

FIELD OF INVENTION

The present disclosure generally relates to robotically controlled surgical systems, and more particularly, to user input devices for directing the movement of elongate surgical instruments to perform minimally invasive diagnostic and therapeutic procedures.

BACKGROUND

Robotic interventional systems and devices are well suited for performing minimally invasive medical procedures as opposed to conventional techniques wherein the patient's body cavity is open to permit the surgeon's hands access to internal organs. Advances in technology have led to significant changes in the field of medical surgery such that less invasive surgical procedures, in particular, minimally invasive surgeries (MIS), are increasingly popular. MIS is generally defined as surgery that is performed by entering the body through the skin, a body cavity, or an anatomical opening utilizing small incisions rather than large, open incisions in the body. With MIS, a patient can experience less operative trauma, reduced hospitalization time, less pain and scarring, reduced incidence of complications related to surgical trauma, lower costs, and a speedier recovery.

A typical manual MIS procedure includes the use of an elongate instrument in the form of a guide wire curved at its distal tip so that the guide wire can be navigated through tortuous anatomy when the guidewire is manipulated by hand at a proximal end by a physician. In addition to linear insertion and retraction, the proximal end can be rolled in the fingertips of the physician to translate a rotational motion to a distal portion of the guide wire. Simultaneous axial insertion and axial rotation of the guidewire achieves spiraling insertion. In addition to the ability to be advanced and rotated to the target site, the guidewire is visible in imaging as a result of its opacity under fluoroscopic imaging. Once the distal end of the guidewire is at the site of the target lesion or vessel segment, another type of elongate instrument in the form of a catheter may be inserted co-axially over the guide wire. The guide wire might then be retracted and removed such that the catheter can remain in place providing a delivery device for other minimally invasive instruments.

Robotic MIS devices and techniques can reduce the time consumed for manual MIS surgical procedures and be less physically demanding on the physician, where manual MIS procedures can not only cause operator fatigue but also excessive exposure to radiation. Medical robotics manufacturers have developed user interfaces to remotely and accurately perform various robot-assisted surgical procedures such as the control of catheters and guidewires in vascular procedures. A typical interface configuration includes a workstation with one or more monitors and one or more user input devices.

Furthermore, robotic MIS devices and techniques have advanced such that elongate catheter instruments may be made steerable at the distal tip. The distal tip may also be controlled by selectively operating tensioning control elements within the catheter instrument, permitting the distal tip to be steered. Steerable catheters may be moved in multiple axes including axial insertion/retraction, axial rotation, deflection/articulation (radial bending) and combinations of these motions. As opposed to steerable catheters, two types of motion are generally associated with non-steerable elongate instruments, i.e., axial insertion/retraction and axial rotation.

A need exists for an input device that is useful to accurately control both steerable and non-steerable elongate instruments. As such, a user input device for a robotic system that can direct movement when steerable devices are attached but also can be optimized for use with non-steerable devices such as guidewires is desirable. Further, robotic input devices that emulate manual procedures are desirable to achieve precise control and physician ease of use. Thus, input device operate in an intuitive manner for both steerable and non-steerable elongate instruments are desirable.

In addition, because the catheter is maneuvered by control motors, a computer, and the like, the surgeon lacks tactile feedback to get an intuitive sense of the location of the distal end of the catheter. Thus to perform certain desired applications, such as, for example, instinctive driving and driving in a fluoroscopy view or a pre-operative model, tactile feedback implemented by haptics to convey information to the physician is further desirable.

SUMMARY

A robotic surgical system includes at least one instrument driver configured to impart axial movement, axial rotation and articulation to an elongate instrument; at least one control computer electrically coupled to the instrument driver to actuate the instrument driver in response to electronic signals; at least one input device having an input shaft configured for movement in at least three dimensions and electrically coupled to the control computer to provide electronic signals to the control computer that corresponds to movement of the input device; wherein the input device is configured to operate in at least two operation modes, with one operation mode that permits movement of the input shaft in at least three dimensions and at least a second operation mode that limits the movement of the input shaft to two dimensions of movement within a plane.

A robotic surgical system includes at least one control computer electrically coupled to an input device and configured to provide haptic signals to the input device; at least one input device operational in two dimensions of movement and configured to direct movement of an elongate instrument and configured to generate haptic effects in response to haptic signals communicated from the control computer; wherein one of the dimensions of movement comprises two operational zones, said operational zones relate to broad and precise linear motion of the elongate instrument and the haptic effects comprise a detent on the border between the two zones.

A robotic surgical system includes at least one control computer electrically coupled to an input device and configured to provide haptic signals to an input device; at least one input device configured to direct movement of an elongate instrument and configured to generate haptic effects in response to haptic signals communicated from the control computer; wherein the haptic effect increases resistance against movement in the axis correlated to rotational actuation of the elongate instrument. The haptic effects can be mapped as a corrugated floor.

Other and further exemplary configurations and advantages thereof will become apparent from the following detailed description when read in view of the accompanying figures.

DETAILED DESCRIPTION

Figure 1:
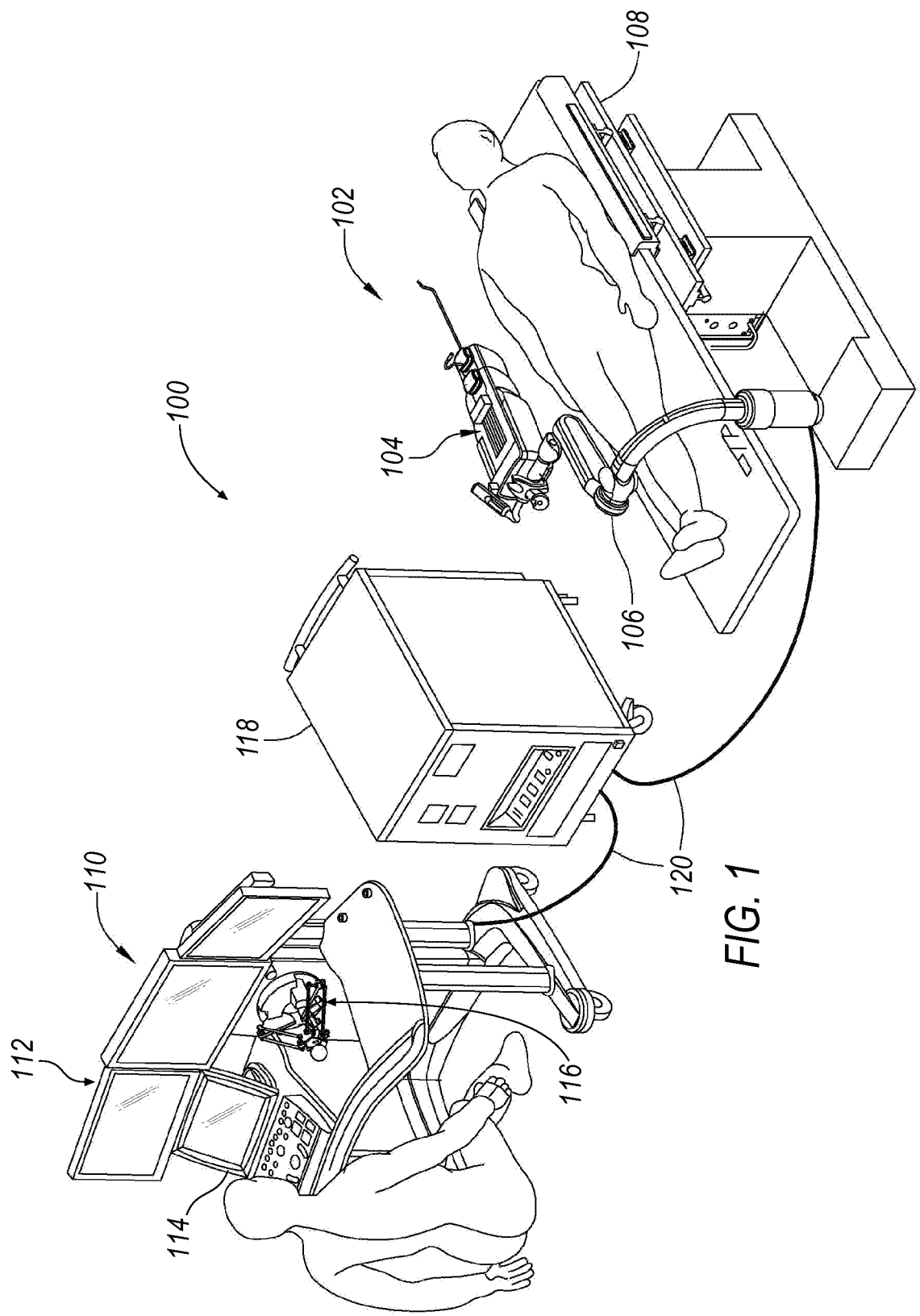
FIG. 1 illustrates a robotic surgical system in an exemplary operation room set up in which apparatus, system and method embodiments may be implemented.

Referring now to the discussion that follows and also to the drawings, illustrative approaches are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Referring to FIG. 1, a robotically controlled surgical system 100 is illustrated in which an apparatus, a system, and/or method may be implemented according to various exemplary illustrations. In the illustrated example, system 100 includes an operator workstation 110, an electronics rack 118, and a robotic instrument assembly 102. The robotic instrument assembly 102 is controllable using a robotic instrument driver assembly 104 (generally referred to as "instrument driver"). During use, a patient is positioned on an operating table or surgical bed 108 (generally referred to as "operating table") to which robotic instrument driver 104 is coupled or mounted by a setup joint mounting brace 106.

Figure 2:
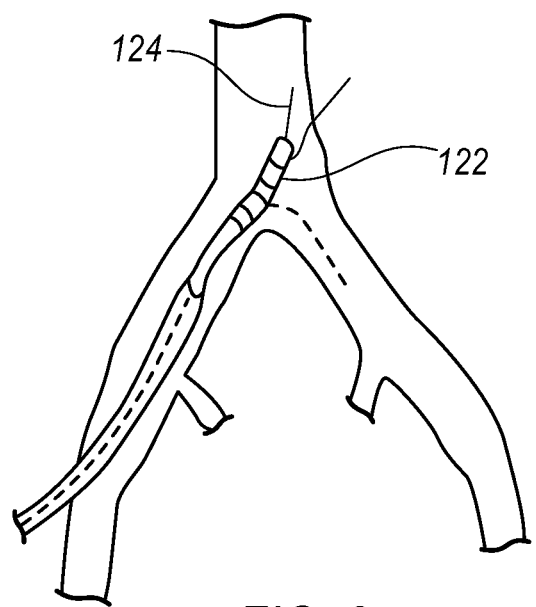
FIG. 2 illustrates elongate instruments inside the lumen of a vessel inside a body.

A surgeon is seated at operator workstation 110 and can monitor the surgical procedure, patient vitals, and control elongate surgical instruments like a guidewire or catheter using one or more user input devices depending upon the surgical procedure. Workstation 110 includes at least one monitor 112, a workstation pendant 114, and at least one user input device 116 which can be a multi-directional joystick apparatus. However, it is understood that other multi-directional user input devices are also contemplated. A monitor 112 may be configured to display a three dimensional object, such as an image of a catheter and/or guidewire in a body cavity or organ, e.g., a chamber of a patient's heart. Referring now to FIG. 2, which illustrates an exemplary image of a surgical procedure, a catheter 122 and a guidewire 124 are shown displayed within or relative to a three dimensional space. In that exemplary image, the distal end of a catheter 122, after insertion in the right common femoral artery a guidewire, is positioned in the right common iliac artery and the guidewire 124 is shown advanced out from the tip of the catheter 122.

Figure 3:
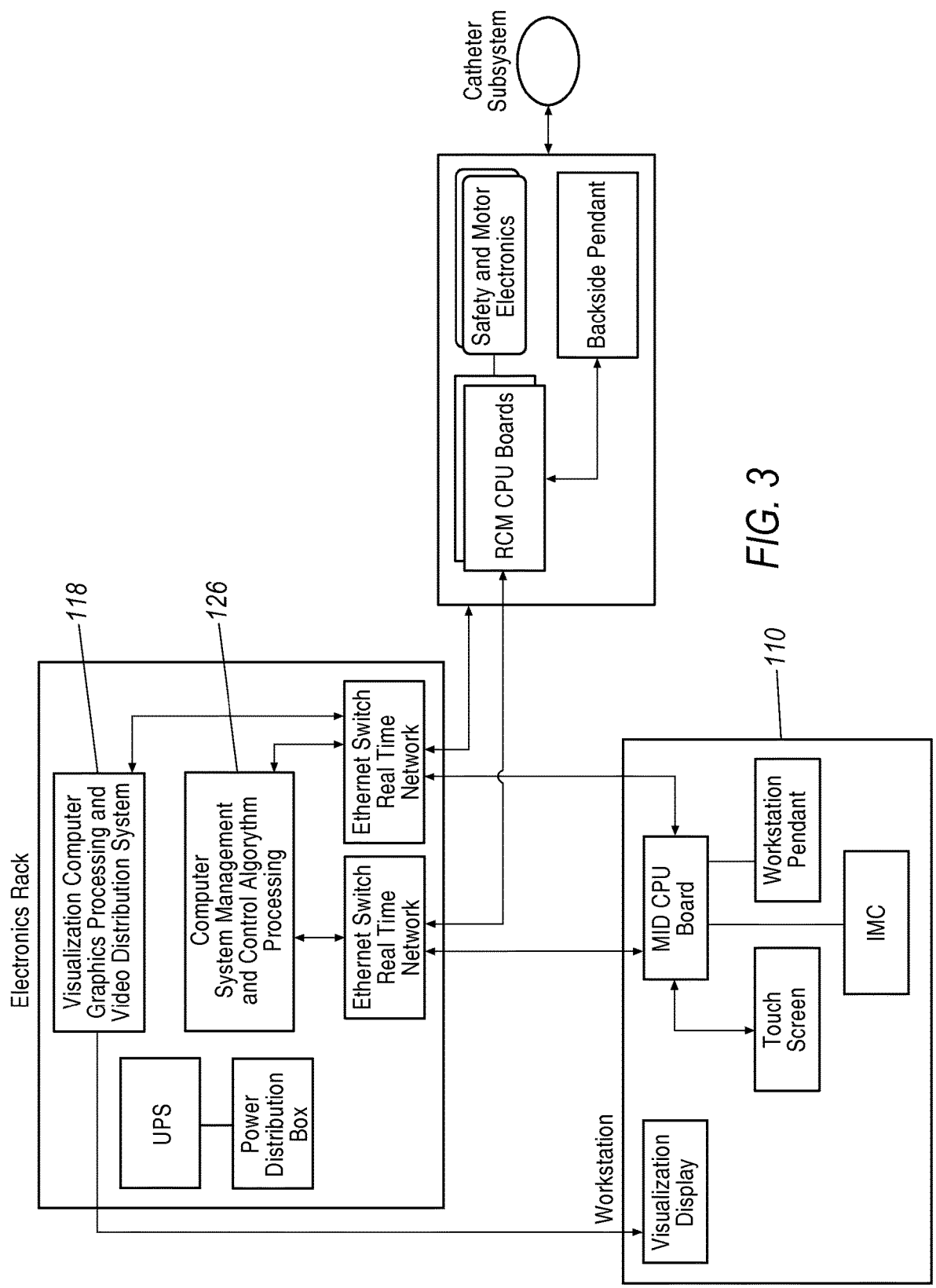
FIG. 3 is a block diagram of an overview of a robotic surgical system.
Figure 4:
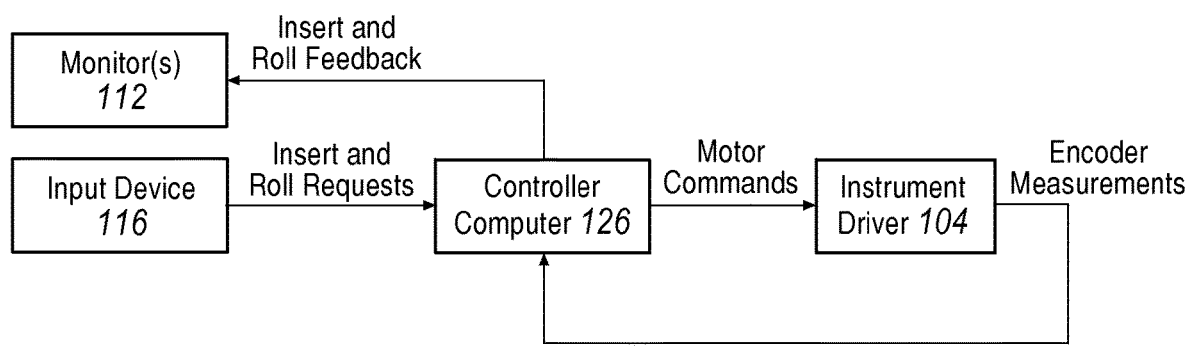
FIG. 4 illustrates a block diagram of the robotic operational responsibilities of the components of an exemplary robotic surgical system.

In the illustrated example, system 100 also includes an electronics rack 118. As shown in the block diagram of an overview of a robotic surgical system in FIG. 3, the electronics rack 118 includes a control computer 126 that performs system management and control algorithm processing. The control computer 126 is electrically coupled to the input devices at the workstation 110 and the instrument driver 104. Control computer 126 translates the desired actions input into the input device into voltages and currents which are applied to the instrument driver 104. The block diagram of FIG. 4 illustrates a flow process between the input device 116 to the control computer 126 to the instrument driver 104. In certain exemplary configurations, the control computer 126 may include haptic processing to convey electronic signals to the workstation 110, and more particularly to the input device 116, to produce tactile feedback to the user. For example, the user input device 116 may provide force feedback if the control computer 126 determines that a command for positioning (advancement, rotation, and/or steering) is inconsistent with a pre-determined operational range or incompatible with information derived from the imaging system. Other haptic feedback methodology is discussed below.

System components may be coupled together via a plurality of cables or other suitable connectors 120 to provide for data communication, or one or more components may be equipped with wireless communication components to reduce or eliminate cables 120. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 5:
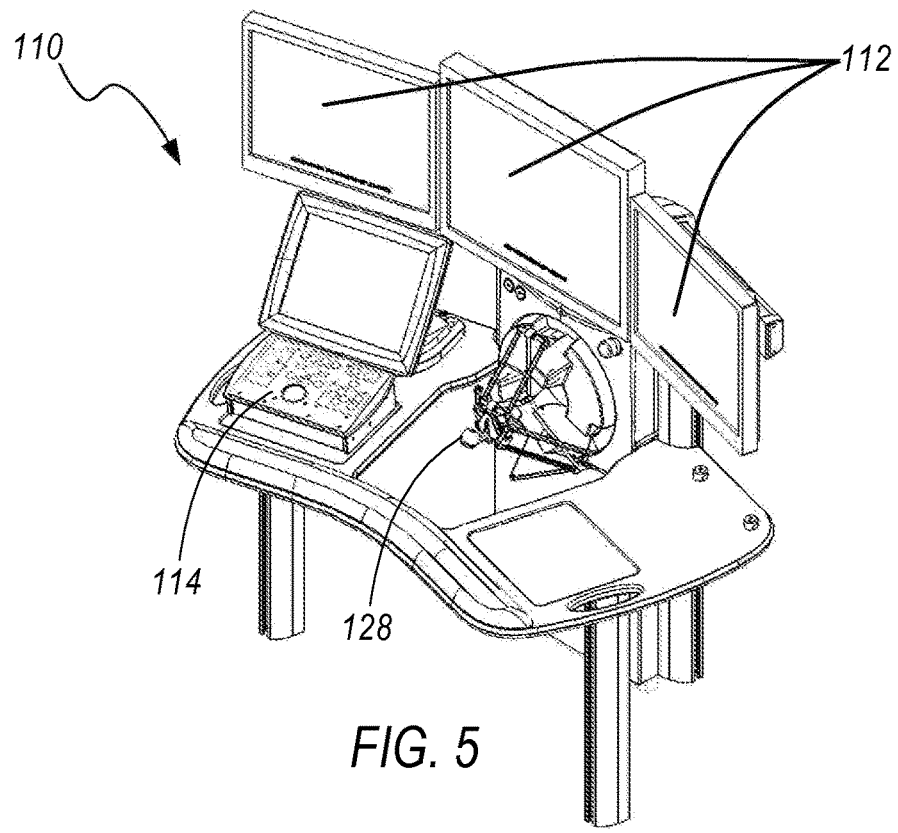
FIG. 5 illustrates an example of an operator workstation of the robotic surgical system.

The operator workstation 110 may further provide for control of the elongate instrument. As one example, shown in FIG. 5 the operator workstation 110 may include a set of controls having a multi-dimensional input device such as joystick 128 and a keyboard type input device such as pendant 114 which may include push buttons, knobs, sliders or the like. A typical workstation may have one or more monitors and one or more user input devices such as a trackball, mouse, joystick, buttons, keys, sliders, thumbwheels, touch screens, stylus and the like.

In a conventional system, the elongate instrument may be controlled using a multi-degree-of-freedom device having multiple joints and associated encoders, such as a joystick type device. A joystick 128 allows for steering of the distal tip of the guide catheter as viewed on the computer monitor display 112, while the guidewire may be controlled using the pendant 114. The joystick 128 may further include various sensors to detect the position of the joystick type controller 128 and to provide signals to the controller that are interpreted as commands. In certain embodiments, the input device may have integrated haptics capability for providing tactile feedback to the surgeon. In that regard, the input device 116 would include motors, actuators or tension rings, e.g., to implement haptic effects by imparting torque, detents, resistance, vibration or other forces to the input device 116.

The elongate instrument may have different configurations in different embodiments. The elongate instrument includes an elongate body having proximal and distal sections. The elongate instrument may be steerable or non-steerable. The elongate instrument may be tubular with a central lumen or solid. An instrument driver 104 may be configured to control two elongate members in a telescopic fashion to thereby advance the elongate instrument inside a body. A variety of elongate instruments could be used in the robotic surgical system, depending upon the surgical procedure and surgeon preference. Exemplary elongate instruments include guidewires, catheters, sheaths, and guide catheters. The elongate instrument can be placed into the drive assembly prior to or during surgery; the instrument driver 104 may be configured to translate and/or rotate the elongate instrument.

Figure 6:
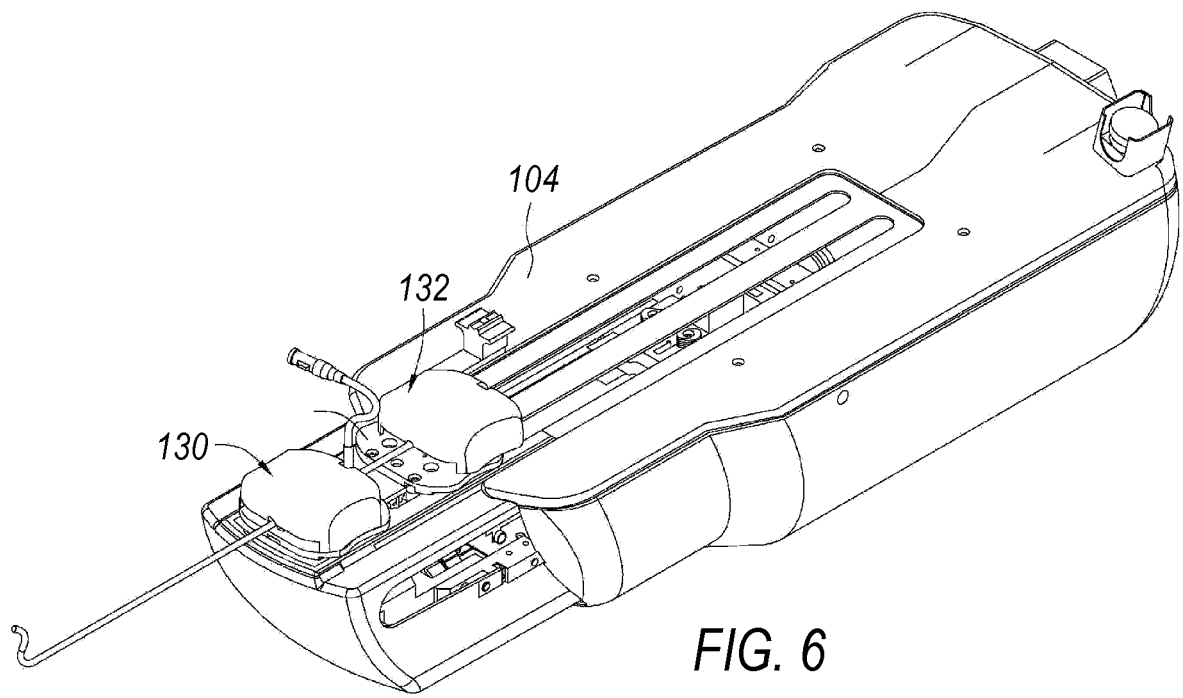
FIG. 6 illustrates an example of an instrument driver capable of imparting three dimensional motion to a steerable elongate instrument.

Referring now to FIG. 6, an embodiment of an instrument driver 104 is shown. The acts of advancing the first elongate instrument and the second elongate instrument may be performed independently or simultaneously so that both the first and second elongate instruments are advanced together. An instrument driver 104 includes a sheath instrument assembly 130 and a catheter instrument assembly 132 mounted on a top portion of instrument driver 104 and arranged in a coaxial manner. Although instruments 130, 132 are arranged coaxially, movement of each instrument can be controlled and manipulated independently. Additional motors in instrument driver 104 may be activated to control bending of the catheter as well as the orientation of the distal tips thereof, including tools mounted at the distal tip.

The distal tip of the catheter instrument may be controlled by selectively operating tensioning control elements within the catheter instrument. In one example, four opposing directional control elements wind their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison. Steerable catheters are controlled using multiple types of motion and in multiple axes, particularly at the tip, including insertion/retraction, rotation, deflection and combinations of these motions. Details of exemplary steerable catheters are disclosed, e.g., in U.S. Pat. No. 8,021,326, the contents of which are incorporated by reference in its entirety.

Some common elongate instruments generally are not and/or do not need to be steerable, such as guidewires, sheaths, and guide catheters. A micro-catheter used to pass through small body lumens is another example of a non-steerable instrument, where it is smaller in diameter than steerable catheters containing driving elements. As opposed to steerable catheters, two types of motion are generally associated with such non-steerable elongate instruments, i.e., axial insertion/retraction and rotation.

Figure 7:
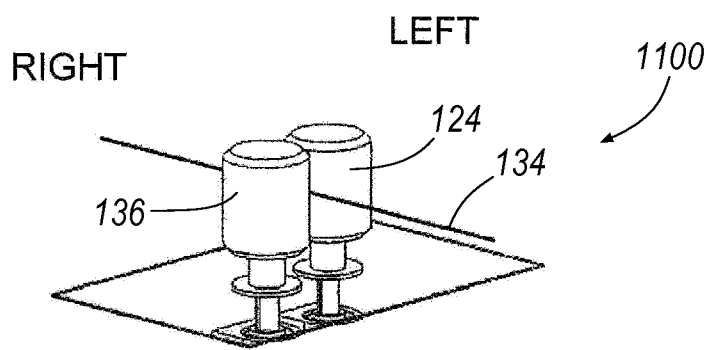
FIG. 7 illustrates an example of an instrument driver capable of imparting linear and axial rotation motion to an elongate instrument.

For some embodiments of the present disclosure, a second instrument driver dedicated to non-steerable elongate instruments may be used. Such drivers need two degrees of freedom: rotation and insertion. One variation of an instrument driver 1100 is shown in FIG. 7. FIG. 7 shows a top view of a pair of feed rollers illustrating how linear and rotation motion can be imparted to the elongate instrument. In accordance with the non-limiting example of this embodiment, the robotic system may include an instrument driver 1100 in which the elongate instrument is a guide wire 134 and is held between first and second rotary member 136, 138. The rotary members can be used to robotically control the insertion and retraction as well as axial rotation of an elongate instrument such as a guidewire along a longitudinal axis of the elongate instrument. To generate a linear motion for insertion and retraction, rotary members are actuated in opposite rotation directions; to generate a rotation motion, the rotary members are actuated in opposite linear directions. The drive assembly may be configured to actuate the rotary members in rotational and linear directions independent of one another or simultaneously. The rotary members may be actuated in the rotational and linear directions at different respective rates. The rotary members are in the form of cylinders or feed rollers in FIG. 7 but the rotary members may include any other device suitable for providing rotary motion including but not limited to belts.

Actuation of the one or more instrument drivers in the present disclosure is directed remotely at the user interface of the workstation 110 using at least one input device. User input devices generally provide good navigation and operational functionality. For example, with a steerable catheter, a surgeon can manipulate the elongate surgical instrument in a plurality of directions using the appropriate input device, including a joystick 128, whereby the surgeon can effect, e.g., insertion/retraction, axial rotation, and multi-directional tip deflection (radial bending). A joystick 128 with multi-dimensional capability allows intuitive manipulation of a physical device and is useful for controlling objects with the same degrees of freedom as the joystick, such as setting the end point position of the tip of a steerable catheter that can travel in three linear orthogonal axes. A joystick 128 can more directly relate hand motion to the expected movement of the elongate instrument.

Robotic systems that are designed with directional control often have more limited capability to rotate the entire elongate instrument, since rotation of the entire instrument is less necessary with a steerable instrument having complete directional control at the tip. In contrast, rotation is crucial for a non-steerable instrument. When a non-steerable instrument is attached to the robotic system, an input device such as a push button on an input pendant 114 has been used to effectuate linear and rotational motion to the non-steerable instrument. With such input pendant 114, two buttons may be dedicated to control insertion and retraction and a second set of buttons may control clockwise and counter-clockwise rotation. In this example for inputting one degree of freedom, holding down of a single first button may cause a motion in a pre-defined direction at a pre-defined speed and release of the button would cease motion.

Guidewires and other non-steerable elongate instruments can be difficult to position and to control due to their relatively minimal navigation degrees of freedom, the need to impart the motion to the proximal end of the elongate instrument, and the tortuous pathways through which operators navigate them. Controlling velocity and controlling coordinated insertion and rotation, however, can be challenging with a push button that is inherently binary. Controlling coordinated motion of the catheter 122 and guide wire 124 using the joystick type controller 128 in combination with the pendant device 114 may also be difficult for operators to perform. For example, to perform a spiraling motion for breaking friction in wire control, the operator may be required to simultaneously push two buttons. Thus such systems may lack the precision desired by operators of the robotic catheter system for performing MIS operations. Furthermore, at times the assumed motion of the instrument does not match the actual motion of the instrument at the proximal end. One reason for this is the presence of unanticipated or un-modeled constraints imposed by the patient's anatomy.

The present disclosure addresses these issues and the need for an input device that is useful to accurately control both steerable and non-steerable elongate instruments. An exemplary embodiment of the present disclosure uses a three dimensional input device such as a joystick 128 to guide both the steerable and non-steerable elongate instruments, whereby the different functionality necessary for the different elongate instruments can be selected at the workstation 110. One exemplary configuration of the present disclosure has two modes of operation where the first mode utilizes conventional joystick-type control of a steerable catheter. The second operational mode restricts the three dimensional input device to two dimensions. Thus, according to an embodiment of the present disclosure, a sub-set of the workspace can be selected to control the manipulator/driver of the non-steerable elongate instrument such as the guidewire or non-steerable catheter.

Figure 8A:
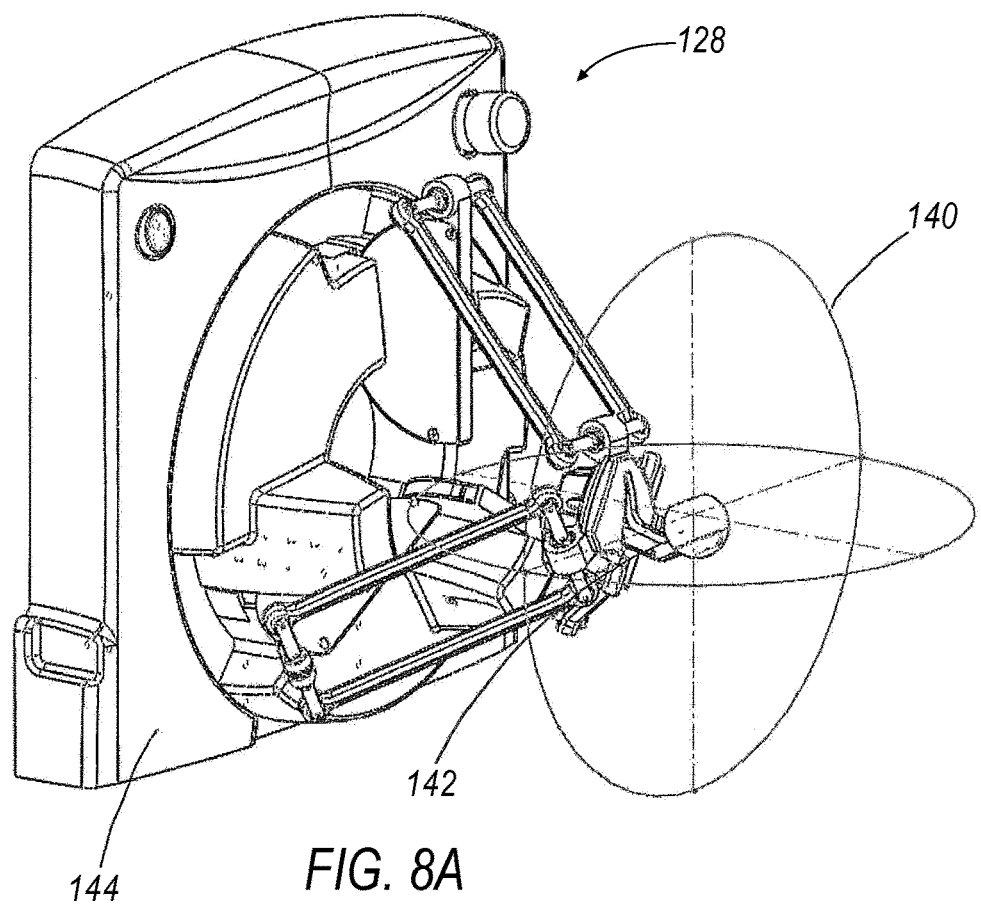
FIG. 8A illustrates a front perspective view of an exemplary input device and a mapping of spherical three dimensional movement.
Figure 8B:
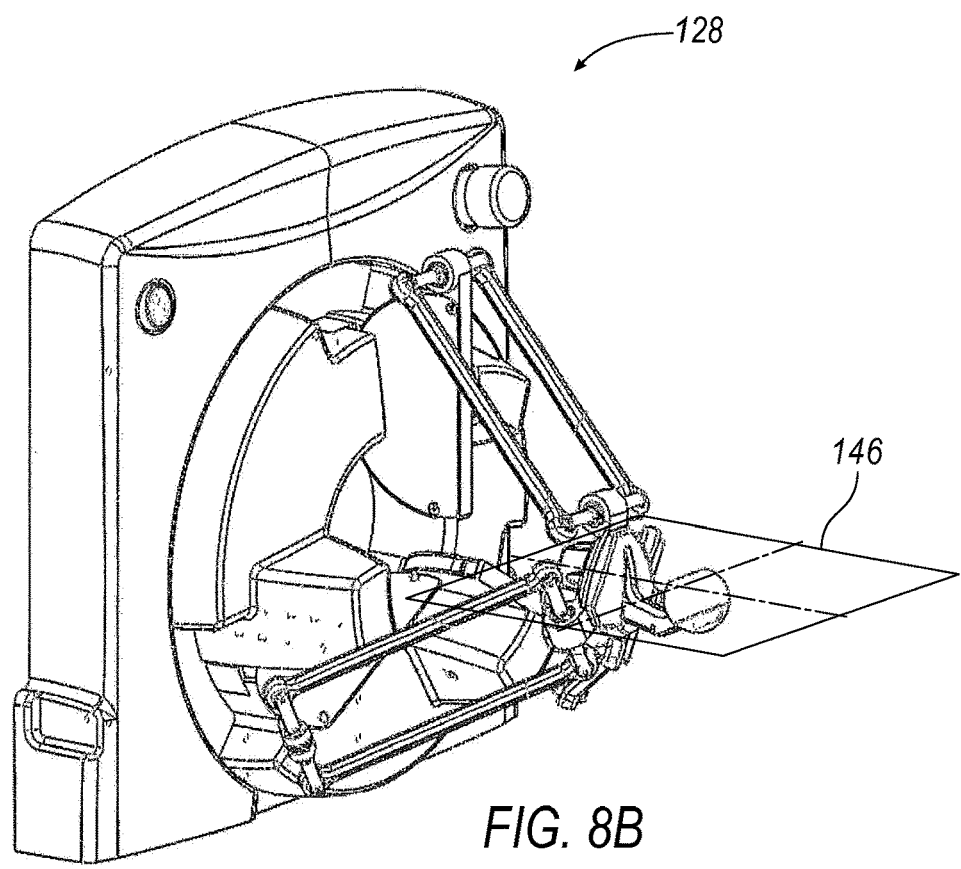
FIG. 8B illustrates a front perspective view of an exemplary input device and a mapping of a plane for two dimensional movement.

Referring now to FIG. 8A, a standard workspace for a three dimensional joystick 128 is a three dimensional sphere, whereby shaft 142 is rotatably coupled to base 144 and configured for motion within a three dimensional workspace 140. As seen in FIG. 8B, the present disclosure contemplates that the workspace of the input device may be selectively restricted to a single plane 146, representing two degrees of freedom, in a second operational mode. In an exemplary configuration, the forward movement of a joystick 128 would correspond to insertion and the backward movement would correspond to retraction of the elongate instrument. In such an embodiment, side to side motion would correlate to rotation in the clockwise or counterclockwise direction. Thus, according to this exemplary embodiment, the joystick 128 is used to selectively control objects with fewer degrees of freedom than the input device while also controlling a non-linear axis. Hence, this exemplary embodiment incorporates the ability to select between two different operational modes on an input device typically used for controlling objects in the X, Y, Z orthogonal planes, where the second operation mode is restricted to the X and Y orthogonal plane for one linear movement (insert/retract) and one non-linear movement (roll). The immediate advantage for the linear aspect of the embodiment is the intuitive position-based control provided to the user; another advantage is the ability to include velocity and acceleration.

Further, by superimposing control of the two axes into one input device 116, complex motions can be commanded with greater ease. Additionally, the joystick 128, as an exemplary input device 116, restores certain kinesthetic information. The present disclosure further contemplates additional embodiments to improve the user's ability to control an elongate surgical instrument like guidewire 124 using a three dimensional joystick 128. With the workspace of the joystick 128 selectively restricted to only a single plane 146, the joystick 128 is amenable to be further enhanced to operate in an intuitive manner for non-steerable elongate instruments, according to additional embodiments discussed below. Robotic input devices that emulate manual procedures are desirable to achieve precise control and physician ease of use. Ease of use can translate to fewer and more confident movement, leading to safer, quicker and more cost effective surgeries, and may enable more difficult procedures.

Because the catheter is maneuvered by control motors, a computer, and the like, the surgeon lacks tactile feedback to get an intuitive sense of the location of the distal end of the catheter. Haptic or tactile feedback can either restore proprioception associated with a manual surgical procedure or even augment the information that would be conveyed to the surgeon in a manual procedure. Thus, the present disclosure not only enables the proprioceptive feedback channel but also has the capability through mapping and haptics to enhance a user's ability to garner information that is available from the control computer as a result of the robotic process. For example, to perform certain desired applications, such as, e.g., instinctive driving and driving in a fluoroscopy view or a pre-operative model, the present embodiment can include information to the physician through tactile feedback implemented via haptic processing by the control computer. The control computer determines the haptic signal and implements the haptic effect by sending haptic signals or commands to one or more motors or other actuators used in the input device. Haptic feedback can include resistance, detents, active push or pull, vibration, and the like. The haptic signals can be varied as function of the position and movement of the input device.

In some exemplary embodiments, the mapping of the workspace can be further modified to enhance dexterity and tactile and visual feedback. Keeping with the example that motion in the forward and backward directions could translate to insertion and retraction of the guidewire and motion in the left and right directions could translate to roll clockwise and roll counterclockwise, this plane can be emphasized or conveyed to the user as a virtual floor and/or ceiling. The user can visualize the position on the virtual floor/ceiling as well as visualize the constraint on the user's ability to manipulate the controller outside of the plane. The image of the actual movement of the elongate instrument can be juxtaposed to the virtual plane to provide additional visual feedback. Mapping schemes can be further overlaid to provide visual feedback concerning joystick positioning and the corresponding positioning of the elongate instrument. The mapping scheme would also be useful for control computer to generate the haptic signals to the input device.

Haptic feedback is also envisioned in certain exemplary embodiments. For example, the joystick can also be used to apply gradually increasing force (or sudden increases) in a certain direction to limit the velocity or acceleration of a user's input such that it does not exceed a pre-determined safe value, or a hardware limitation. In addition the kinesthetic channel allowed for by the use of this multidimensional joystick can be used to provide additional information to the operator, thereby improving the operability of a joystick for two dimensional movement. For example, when the limits of rotation of either axis has been reached, a left or right virtual wall can be erected to prevent the operator from attempting to travel any further in that direction and informing them of this limitation in a non-visual way.

Further, in one exemplary arrangement, the virtual work space can include multiple zones and tactile feedback to address the different needs associated with navigating the elongate instrument through the anatomy of a patient in contrast to robotically manipulating a guide sheath and inner catheter at a work site. As seen in the illustration of a mapping in FIG. 9, different zones, positioned at the front and back boundary of the workspace, can be designed for different types of control. These zones can be separated by virtual detent forces that need to be overcome to cross from one zone to the next. This is useful for when making long insertion motions and eliminates the need to re-clutch multiple times. The presence of a virtual detent 150 requires the user to make a full stop before moving onto a velocity control zone 148. This allows a velocity controller to linearly scale the velocity based on the amount of penetration into the velocity control zone, effectively starting at zero velocity at the detent location 150 and reaching the maximum allowable velocity at the outer end of the velocity control zone 148. In this manner, once the shaft of the joystick is pushed forward over the detent 150, the velocity control zone 148 is active. Once the wire is located at the general target site, precise motion control is desirable and the shaft of the joystick can be position in the precision control 149.

Figure 9:
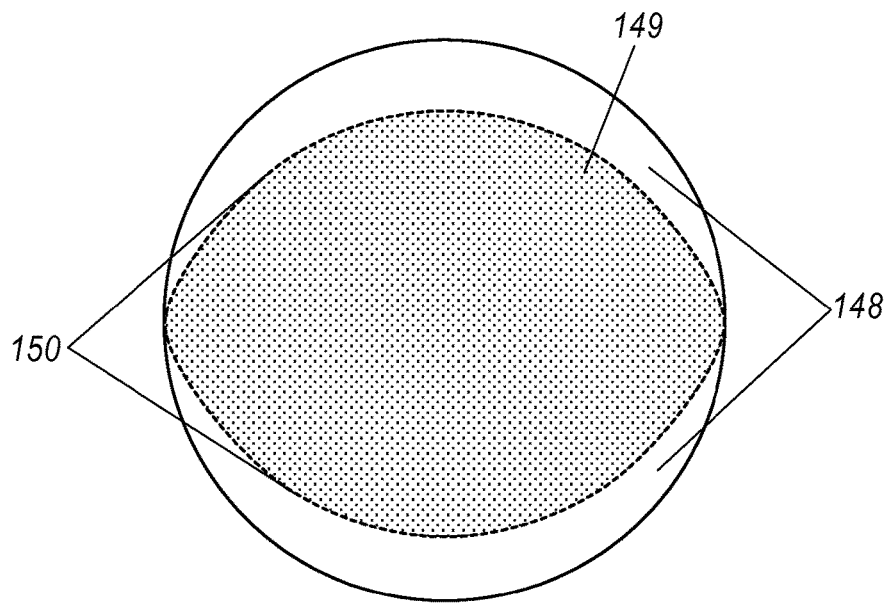
FIG. 9 illustrates an alternate mapping of a plane of movement with a plurality of operational zones.

In one optional aspect of the embodiment, the velocity control zone may be expanded to the middle of the position control zone when retracting, so that the user can switch back to position control when he or she reaches the middle of the workspace. In the embodiment as depicted in FIG. 9, only linear insertion/retraction is subject to the dual zones whereas a single rotation zone extends to the boundary of the workspace. Of course, control of the axis does not need to be limited to purely position or velocity based.

Another optional embodiment would include scaling techniques to enable finer control for the operator. In this non-limiting example, inputs further away from the origin (clutch-point) may be scaled to correspond to greater motion. In that embodiment, the driving mode would be such that for large motions, large sweeps of the input device should be made but frequent re-clutching would be performed to maintain commands close to the origin for finer control. Another embodiment is to use the instantaneous velocity and/or acceleration of the user's input to dynamically scale the amount of output motion, with the assumption that a faster (more aggressive) motion indicates that greater motion is desired.

In one exemplary embodiment, tactile feedback is added to either guide motion so as to eliminate roll being unintentionally commanded or to provide a sensory communication to the surgeon of the amount of roll being imparted to the input device. Haptic forces could be applied to the input device in the form of a centering force to assist the user in moving predominantly in only one axis without precluding simultaneous motion. This force could be overcome by the user (such as a detent) to enable simultaneous motion in both axis. In addition, the magnitude of the resistive force could be scaled based on the velocity of the input. One technique for this embodiment would contemplate force impediments for faster, larger motions to be restricted but slower, finer motion would be impediment-free so that the user is free to combine distinct input modes such as insert and roll in that approach. One advantage of this embodiment is the assistance of insertion and retraction without accidental rolling of the guidewire.

Figure 10:
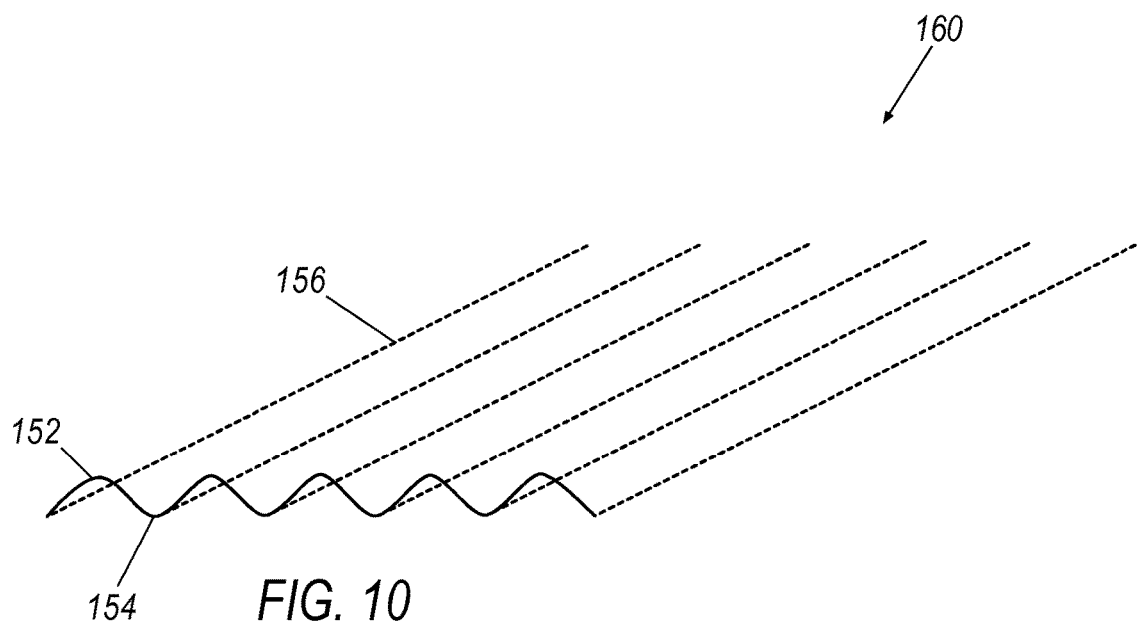
FIG. 10 illustrates an alternate mapping of haptic resistance mapped to a virtual corrugated floor.

As illustrated in FIG. 10, one exemplary aspect of such an embodiment could take the form of a virtual corrugated floor 160 having peaks 152 and valleys 154. In guiding the input device, the input device would freely move in one axis (that could represent linear motion) but face increasing resistance to movement in the second axis (that could represent rotation) until reaching the peak 152. Peak 152 represents a detent which provides feedback to the surgeon that a predetermined angular rotation was effected. The centering force in the insert/retract direction could be applied keeping the motion in the valley 154 to further assist the surgeon in effecting linear motion without unintended roll. The force or heights of the corrugation peaks should be set sufficiently low to retain the ability to perform simultaneous motions. This optimizes the ability to direct insertion without unintended rolling of the guidewire but without entirely removing the ability to command a spiral insertion when desired.

Accordingly, in this embodiment, the corrugations allow a user to "feel" the amount of roll has been commanded and provide haptic feedback on the amount of roll commanded. In a manual surgery, the surgeon has a tactile sense of the amount that he or she has rolled the proximal end of the guidewire, and thus this embodiment would restore a sense of the amount of rotation imparted robotically to better mimic the tactile feedback of a manual surgery. This is important to avoid potential guidewire whip at the distal end of the guidewire, which occurs when rotation at the proximal end of the guidewire has not translated to the distal end due to friction as a result of tissue contact or the bending of the guidewire within the anatomy of the patient. Once the friction is overcome by the build-up of torque in the guidewire, the distal end of the guidewire may whip around. By knowing the amount of rotation imparted on the guidewire—e.g., crossing four detents each representing a 90 degree turn would be a full rotation—the surgeon can recognize based on guide wire tip movement if wind-up is occurring and that further rolling of the guide wire should be avoided.

This embodiment could be implemented with many variations. For example, the frequency (corresponding to angular rotation) and amplitude (corresponding to peak height) of the virtual corrugated floor can be pre-determined or selectable by the surgeon. Similarly, the magnitude of the resistance to motion or detents for haptic feedback can be varied. The proportionality of the haptic feedback may be user selectable. Further, the frequency and amplitude could be variable. For one exemplary embodiment, the amount of force to overcome the detent and reach the next valley could be increased every periodic detent to give a second signal the surgeon of the amount of rotation. One example would be that the periodic detent of greater resistance force would represent one full turn or selectable number of turns. Another exemplary embodiment would gradually increase the height of the peaks as more rotation was imparted on the guidewire.

In one exemplary embodiment, the user could select between movement on a plane with or without corrugations. A user could select from multiple levels/floors to enable different types of centering forces. Selection could be made in a conventional fashion via switches, touchscreens, buttons or the like. Alternatively, switching could be made along the Z-axis which is not utilized for motion commands. The embodiment could be configured to permit the user to lift the controller upwards to pop into a second floor with corrugations a flat floor without any corrugation, a floor with corrugations running in opposite directions, or another scheme.

In another embodiment, similar to the virtual corrugated floor, a virtual ruler can be deployed to restrict user motion in a single direction, effectively decoupling the two modes of operation. In the contemplated embodiment, the virtual ruler would not be in active state all the time but only deployed on a need basis. For example, the virtual ruler would allow the user to perform insertion without being affected by inadvertent roll motion and can be used in conjunction with the virtual corrugated floor, which provides valuable kinesthetic feedback regarding the amount of roll.

Figure 11:
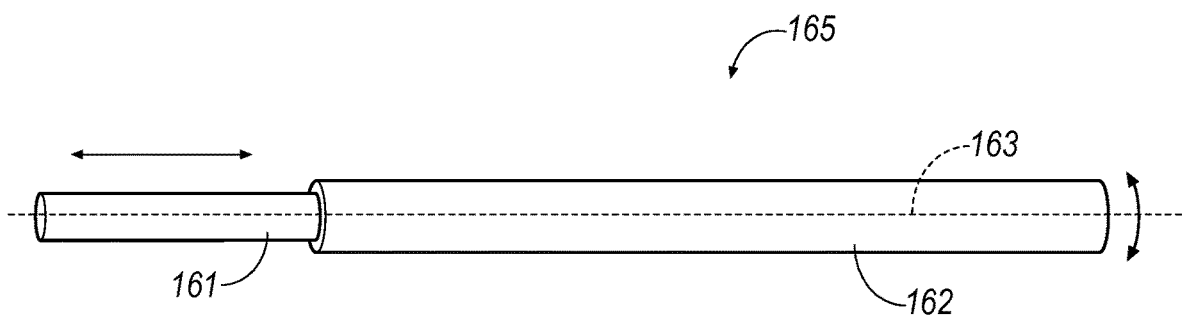
FIG. 11 illustrates an alternative input device for a non-steerable instrument.

The use of haptic forces in the form of resistance or detents is applicable to many types of input devices. For example, a pen-type input device is contemplated within the present disclosure, an example of which is shown in FIG. 11. The pen device 165 for manipulating the position and orientation of an elongate instrument includes an inner member 161 and an outer member 162. The inner member 161, as illustrated, has a generally cylindrical shape that defines an axis 163. The outer member 162 is coaxially disposed on the inner member 161 and is configured to rotate about and move along the axis 163. This movement of the outer member 162 relative to the inner member 161 may be detected and signals the user's desired operation of the elongate instrument. Specifically, rotating the outer member 162 about the axis 163 may indicate the desire to rotate the elongate instrument whereas moving the outer member 162 along the axis 1163 may indicate the desire to advance or retract the elongate instrument relative to the patient. Similar to the haptic feedback provided to the joystick type input device, the rotation control and/or the insertion control can be selected from a variety of options including but not limited to unrestricted movement, increasing resistance, and periodic movement limitations in the form of increased resistance or detents. Further, in an exemplary embodiment, detents could be employed to represent a predetermined angular rotation of the rotation controller. Another variation would permit the predetermined angular rotation to be selectable by the user.

For certain variations of the instrument driver, the capability of measuring external force applied to the distal end of the elongate instrument, e.g., a guidewire, may be desirable. Thus, if a distal tip of the guidewire makes contact with tissue, the user could be made aware of the force being applied to the tissue where the instrument driver includes a variation force sensing during insert/retract and roll actuation. In yet another embodiment, the haptics capability may be implemented in conjunction with catheter position using Fiber Optic Shape Sensing and Localization (FOSSL), which is a technology that can sense the shape of a flexible body such as a catheter during a surgical procedure to permit visualization of the catheter in the patient's anatomy.

The different driving modes and/or different combinations of driving modes are advantageous in allowing an elongate instrument (catheter, sheath, guidewire) to access any part of the vasculature. In some embodiments, the system described herein may be used to treat thoracic aneurysm, thoracoabdominal aortic aneurysm, abdominal aortic aneurysm, isolated common iliac aneurysm, visceral arteries aneurysm, or other types of aneurysm. Embodiments of the system described herein may be used to deliver any substance into a patient's body, including but not limited to contrast (e.g., for viewing under fluoroscope), drug, medication, blood, etc. In further embodiments, the system described herein may be used to access renal artery for treating hypertension, uterine artery fibroids, atherosclerosis, and any peripheral artery disease. In still further embodiments, the system described herein may be used to access any part of a digestive system ore respiratory system.

Operator workstation 112 may include a computer or a computer readable storage medium. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A robotic control system, comprising:
   at least one input device moveable in at least two dimensions within a workspace that comprises a first zone and a second zone; and
   at least one control computer electrically coupled to the at least one input device, the at least one control computer comprising:
     a computer-readable memory having stored thereon executable instructions, and
     a processor in communication with the computer-readable memory and configured to execute the instructions to direct movement of an elongated instrument in response to a position of the at least one input device by at least:
       directing the elongate instrument to move in a direction based on the position of the at least one input device when the at least one input device is positioned within the first zone, and
       when the at least one input device is positioned out of the first zone and in a second zone, directing the elongate instrument to move in the direction at a velocity scaled to the position of the at least one input device within the second zone and changing the velocity scale based on the position of the at least one input device within the second zone such that velocity of the elongated instrument changes based on the amount of penetration into the second zone, wherein a maximum velocity occurs at an outer end of the second zone.

2. The robotic control system of claim 1,
   wherein the at least one control computer is configured to provide haptic signals to the at least one input device,
   wherein the at least one input device is configured to generate a haptic effect in response to the haptic signals communicated from the at least one control computer, and
   wherein the haptic effect comprises an increased resistive force against movement of the at least one input device in at least one of the at least two dimensions.

3. The robotic control system of claim 2, further comprising a floor having a plurality of peaks and valleys to which the haptic signals are mapped to control generation of the haptic effect, wherein the resistive force increases when approaching each of the plurality of peaks and decreases when approaching each of the plurality of valleys.

4. The robotic control system of claim 1, wherein the at least one input device comprises a joystick.

5. The robotic control system of claim 1, wherein the at least one input device comprises:
   an inner member defining an axis; and
   a cylindrical outer member coaxially disposed about the inner member, the outer member being rotatable about and moveable along the axis.

6. The robotic control system of claim 1, wherein movement of the at least one input device in a second dimension of the at least two dimensions is characterized by increased resistance until a peak resistance is reached.

7. The robotic control system of claim 6, wherein the at least one input device and the at least one control computer are configured to impart a predetermined amount of rotation to the elongate instrument when the peak resistance is overcome.

8. The robotic control system of claim 1, wherein the at least one input device is configured to provide electronic signals to the at least one control computer corresponding to movement of the at least one input device.

9. The robotic control system of claim 1, wherein the at least two dimensions of the at least one input device correspond to linear movement and axial rotation of the elongate instrument.

10. The robotic control system of claim 1, further comprising at least one instrument driver configured to impart axial movement, axial rotation, and articulation to the elongate instrument.

11. The robotic control system of claim 1, further comprising at least one monitor to output imaging information.

12. The robotic control system of claim 1, wherein the at least one input device comprises an input shaft configured for movement in three dimensions.

13. The robotic control system of claim 12, wherein the at least one input device is configured to operate in at least two operation modes, with a first operation mode that permits movement of the input shaft in at least three dimensions and a second operation mode that limits the movement of the input shaft to two dimensions of movement within a plane.

14. The robotic control system of claim 12, wherein movement of the input shaft in a third dimension switches the robotic surgical system between virtual maps related to one of linear motion control, haptic feedback, or a combination of linear motion control and haptic feedback.

15. The robotic control system of claim 2, wherein the resistive force creates a haptic detent that represents a predetermined angular rotation of the elongate instrument when the at least one input device is moved along a second dimension of the at least two dimensions.

16. A robotic control system, comprising:
at least one input device moveable in at least two dimensions within a workspace that comprises a first zone and a second zone; and
at least one control computer electrically coupled to the at least one input device, the at least one control computer comprising:
  a computer-readable memory having stored thereon executable instructions, and
  a processor in communication with the computer-readable memory and configured to execute the instructions to direct movement of an elongated instrument in response to a position of the at least one input device by at least:
    directing the elongate instrument to move in a direction based on the position of the at least one input device when the at least one input device is positioned within the first zone, and
    when the at least one input device is positioned out of the first zone and in a second zone, directing the elongate instrument to move in the direction at a velocity scaled to the position of the at least one input device within the second zone and changing the velocity scale based on the position of the at least one input device within the second zone such that velocity of the elongated instrument changes based on the amount of penetration into the second zone,
  wherein movement of the at least one input device in a second dimension of the at least two dimensions is characterized by increased resistance until a peak resistance is reached.

17. The robotic control system of claim 16, wherein the at least one input device and the at least one control computer are configured to impart a predetermined amount of rotation to the elongate instrument when the peak resistance is overcome.

18. The robotic control system of claim 16,
  wherein the at least one control computer is configured to provide haptic signals to the at least one input device,
  wherein the at least one input device is configured to generate a haptic effect in response to the haptic signals communicated from the at least one control computer, and
  wherein the haptic effect comprises an increased resistive force against movement of the at least one input device in at least one of the at least two dimensions.

19. The robotic control system of claim 18, wherein the resistive force creates a haptic detent that represents a predetermined angular rotation of the elongate instrument when the at least one input device is moved along a second dimension of the at least two dimensions.

20. The robotic control system of claim 18, wherein the resistive force creates a haptic detent to separate the first zone and the second zone, wherein a zero velocity occurs at the haptic detent.

* * * * *